United States Patent
Ware et al.

(10) Patent No.: US 9,848,857 B2
(45) Date of Patent: *Dec. 26, 2017

(54) WIRELESS FOOT CONTROLLER

(71) Applicant: LINVATEC CORPORATION, Largo, FL (US)

(72) Inventors: Michael Ware, Tampa, FL (US); Ronald Reinhart, Oldsmar, FL (US)

(73) Assignee: LINVATEC CORPORATION, Largo, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/001,060

(22) Filed: Jan. 19, 2016

(65) Prior Publication Data
US 2016/0128678 A1  May 12, 2016

Related U.S. Application Data

(62) Division of application No. 12/313,991, filed on Nov. 25, 2008, now Pat. No. 9,265,518.

(51) Int. Cl.
*A61B 17/00* (2006.01)
*A61B 17/32* (2006.01)
(Continued)

(52) U.S. Cl.
CPC ........ *A61B 17/00* (2013.01); *A61B 17/32002* (2013.01); *A61B 90/08* (2016.02);
(Continued)

(58) Field of Classification Search
CPC ... A61B 17/00; A61B 10/08; A61B 17/23002; G08C 17/02
See application file for complete search history.

(56) References Cited

U.S. PATENT DOCUMENTS 9,265,518 B2 * 2/2016 Ware ................. A61B 17/32002
2006/0116667 A1 * 6/2006 Hamel ............ A61B 17/320068
606/1

OTHER PUBLICATIONS

Gascon (Wireless Sensor Networks Research Group, sensor-networks.org/index.php?page=0823123150. Published Nov. 17, 2008; 4 pages, last accessed Feb. 7, 2013).*
(Continued)

*Primary Examiner* — Cherie M Stanfield
(74) *Attorney, Agent, or Firm* — Frederick J M Price; Bond, Schoeneck & King, PLLC

(57) ABSTRACT

The invention includes systems and methods for controlling devices including surgical instruments using a wireless footswitch. The systems of the invention include a wireless footswitch, a footswitch adapter, and an electric console for powering and controlling surgical instruments. The systems of the invention further include a wireless footswitch for controlling battery powered surgical instruments. The methods of the invention include syncing a wireless footswitch with a controlled device or a wireless footswitch adapter using a lower power wireless mode, then signaling the controlled device or wireless footswitch adapter using a higher power wireless mode. The systems and methods of the invention include using a wireless device or wireless footswitch adapter to monitor transmissions from other wireless devices to prevent syncing with the wireless footswitch adapter using the same channel or network identification as other wireless devices or wireless footswitch adapters.

10 Claims, 6 Drawing Sheets

(51) Int. Cl.
*A61B 90/00* (2016.01)
*G08C 17/02* (2006.01)
(52) U.S. Cl.
CPC .... *G08C 17/02* (2013.01); *A61B 2017/00221* (2013.01); *A61B 2017/00225* (2013.01); *A61B 2017/00973* (2013.01); *G08C 2201/30* (2013.01); *Y02B 60/50* (2013.01)

(56) References Cited

OTHER PUBLICATIONS

Daintree Networks (Understanding 802.15.4 and ZigBee Networking. 2005; www.daintree.net/downloads/whitepapers/understanding_sensor_networking_whitepaper.pdf; 8 pages, last accessed Feb. 7, 2013).*

* cited by examiner

WIRELESS FOOT CONTROLLER

This application is a divisional application of U.S. application Ser. No. 12/313,991 filed Nov. 25, 2008. The entire disclosure of prior application is herewith incorporated by reference.

BACKGROUND OF THE INVENTION

1. Technical Field

This invention relates to a wireless foot controller that may be used to control devices including medical devices.

2. Description of the Prior Art

Many applications can benefit from hands-free control, and in particular, many surgical applications can benefit by allowing control of surgical instruments without requiring the instruments' operators to use their hands to control the instruments. There have been several applications in the prior art that use footswitches or foot pedals to control surgical instruments. However, many of these applications use wired connections between the controller and the controlled device. This hardwired arrangement suffers many problems, however, including requiring multiple controllers to control multiple devices, safety hazards from floor to table wiring, and requiring additional effort to maintain a sterile environment.

To address these problems, some applications offer wireless control of devices. For example, U.S. Pat. No. 7,428,439 (Reynolds et al.) describes a wireless foot control system using infrared signaling between the transmitter and the receiver in the controlled device. However, infrared signaling can be problematic because it typically requires the transmitter to be within the line of sight of the receiver or at least requires particular arrangements of the transmitter and receiver that may be inconvenient in practice.

Other wireless foot controllers use radiofrequency signaling, which does not require a line of sight arrangement between the transmitter and receiver. However, these applications frequently suffer from interference from other radiofrequency-emitting devices and thus tend to have problems associating (i.e., bonding or syncing) the controller with a controlled device, particularly where a single controller is used to control multiple devices. One attempt to overcome this problem is described in U.S. Patent Application Publication No. 2007/0249286 (Ma et al.), which describes a system and method for associating a wireless transmitter to multiple wireless devices. But this application requires first establishing a wired connection to each of the controlled devices in order to associate the device with the controller. This extra step of physically connecting the device to the controller is inconvenient and may compromise the sterility of a controlled surgical instrument. U.S. Patent Application Publication No. 2008/0140158 (Hamel et al.) describes a wireless foot controller capable of controlling multiple devices using the Bluetooth or IEEE 802.11a, b, g, 802.12 or 802.16 wireless standards. However, this approach also suffers from problems associating the controlled device with the controller, and typically requires bringing each controlled device into close proximity to the controller in order to associate ("sync") the controlled device with the controller. As with the wired association solution, this approach is inconvenient and may compromise the sterility of a controlled surgical instrument.

Thus there exists a need in the art for a wireless foot controller capable of controlling multiple devices, and capable of associating with controlled devices without requiring a physical connection or close physical proximity between the controller and the controlled devices.

SUMMARY OF THE INVENTION

The invention includes an apparatus for controlling the operation of a surgical device comprising a first wireless transceiver configured to receive a connect signal while in a low power mode and, in response to the connect signal, to transmit low power wireless sync signals, and further configured to receive a wireless sync acknowledgement signal and to place the apparatus into a synced state, and a pedal configured to be operated by a foot of a user and to provide a pedal signal, the first wireless transceiver further configured to generate, when the apparatus is in a synced state, a higher power mode wireless signal in response to the pedal signal, wherein the wireless signal controls the operation of the surgical device. The apparatus may further comprise a sync button, wherein the sync button is configured to provide the connect signal to the first wireless transceiver. The surgical device may comprise a second wireless transceiver and a sync button, wherein the sync button is configured to provide the connect signal to the first wireless transceiver. In addition to or instead of the surgical device comprising a second wireless transceiver, the apparatus may comprise a wireless footswitch adapter comprising a wireless transceiver and sync button, wherein the sync button is configured to provide the connect signal to the wireless transceiver. In embodiments with a wireless footswitch adapter, the apparatus may further comprise an electric console for providing power and wired control signals to the surgical device, wherein the wireless footswitch adapter receives the higher power mode wireless signal in response to the pedal signal and transmits a wired signal representative of the higher power mode wireless signal to the electric console.

The invention includes a system for wirelessly controlling a surgical instrument comprising a wireless footswitch comprising a first wireless transceiver and a pedal configured to be operated by a foot of a user and to provide a pedal signal in response, wherein the pedal signal is converted to a control signal transmitted by the first wireless transceiver; a surgical instrument or a wireless footswitch adapter with a second wireless transceiver; wherein the first wireless transceiver is configured to transmit sync signals in a lower power mode and, upon syncing between the first and second wireless transceivers, the first wireless transceiver transmits control signals in a higher power mode. The wireless footswitch adapter may be operatively connected to an electric console and transmit control signals to the electric console, wherein a surgical instrument has a wired connection to the electric console for receiving the control signals from the electric console.

The invention includes a method for controlling a surgical instrument comprising providing a wireless footswitch with a first wireless transceiver, a wireless footswitch adapter with a second wireless transceiver, an electric console operatively connected to the wireless footswitch adapter, the surgical instrument being operatively connected to the electric console; transmitting a sync signal from the wireless footswitch in a lower power sync mode to the wireless footswitch adapter; receiving a pedal signal at the wireless footswitch, wherein the pedal signal is provided by depressing a pedal on the wireless footswitch; processing the pedal signal at the wireless footswitch to generate a control signal; transmitting the control signal wirelessly in a higher power mode to the wireless footswitch adapter; transmitting the control signal from the wireless footswitch adapter to the electric console; processing the control signal at the electric console; and controlling the surgical instrument in accordance with the control signal. The electric console may be operatively connected to a plurality of surgical instruments, and the plurality of surgical instruments may be controllable with said wireless footswitch.

In another aspect, the invention includes a method for controlling a surgical instrument comprising providing a wireless footswitch comprising a first wireless transceiver and the surgical instrument with a second wireless transceiver; transmitting a sync signal from the wireless footswitch in a lower power sync mode to the second wireless transmitter; receiving a pedal signal at the wireless footswitch, wherein the pedal signal is provided by activating a pedal on the wireless footswitch; processing the pedal signal at the wireless footswitch to generate a control signal; transmitting the control signal wirelessly in a higher power mode to the second wireless transceiver; processing the control signal at the surgical instrument; and controlling the surgical instrument in accordance with the control signal. The wireless footswitch may be synced to a plurality of surgical instruments, and the wireless footswitch may control one of the plurality of surgical instruments synced to the wireless footswitch.

In each of the embodiments of the invention, the lower power mode may be adjusted to a power that allows syncing the wireless footswitch with a wireless footswitch adapter within a predetermined distance from the wireless footswitch, e.g., in the same room as the wireless footswitch, and does not allow syncing the wireless footswitch with a wireless footswitch adapter beyond the predetermined distance, e.g., outside of the room with the wireless footswitch. The lower power mode may be in the range of about −16.2 dBm and about −7.0 dBm and the higher power mode may be in the range of about −0.7 dBm and about +1.4 dBm. The wireless transceivers in the surgical instrument and/or wireless footswitch adapter may remain in a higher power mode and monitor transmissions from a third wireless transceiver, and wherein when the second wireless transceiver detects a signal from the third wireless transceiver, the second wireless transceiver detects channel and network identification information from the third wireless transceiver, the channel and network identification information being excluded from the possible channels and network identifications available for use when syncing the second wireless transceiver to the first wireless transceiver. The wireless transceivers in the wireless footswitch, the wireless footswitch adapter, and/or the surgical instrument may be IEEE 802.15.4 wireless transceivers using Zigbee network stack communication protocols.

DETAILED DESCRIPTION OF THE INVENTION

Figure 1:
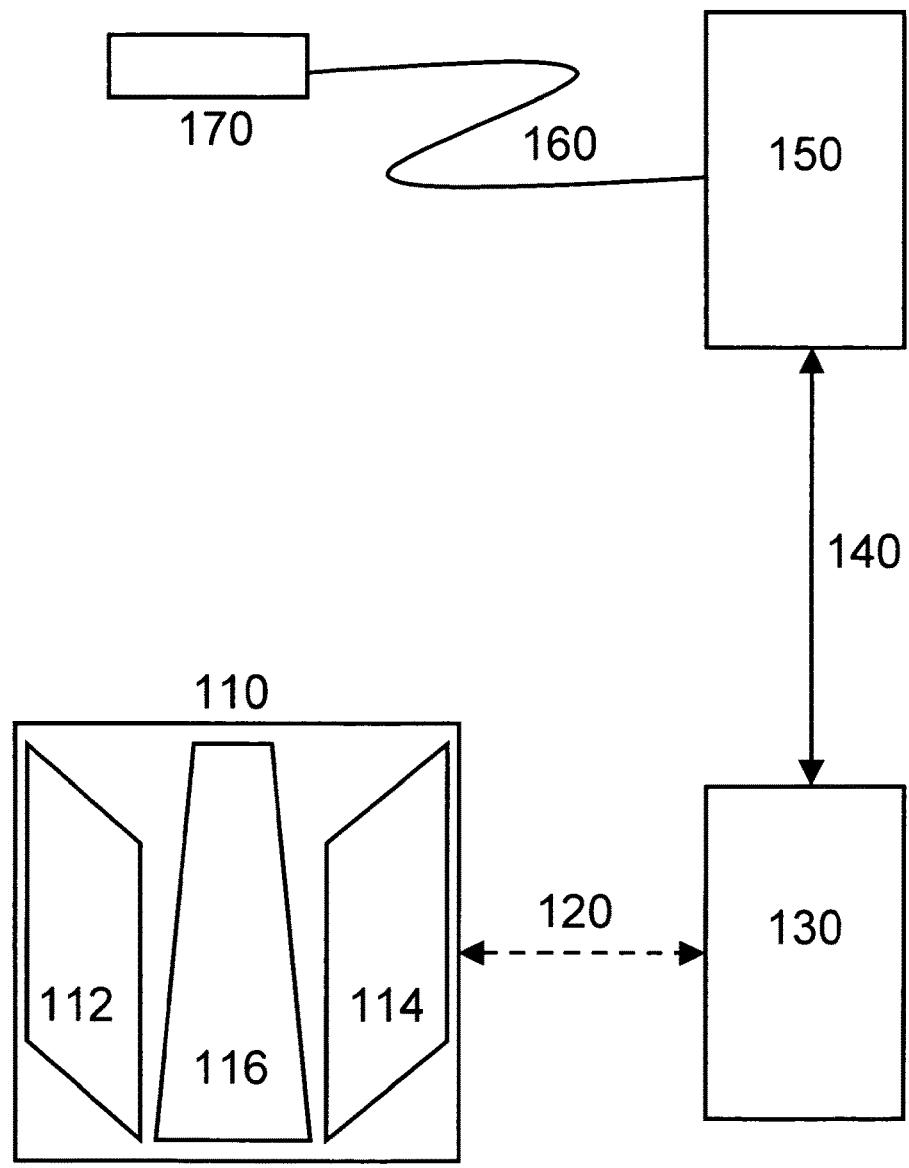
FIG. 1 is a block diagram showing an embodiment of the invention that includes a wireless footswitch adapter with an electric console.

The invention includes wireless devices and methods for syncing and communicating between wireless devices. In a preferred embodiment, the invention includes a wireless footswitch device with a wireless transceiver capable of controlling multiple devices each having a wireless transceiver. As used herein, the term "footswitch" includes any controller device operable by foot, including, for example, toggle switches, pushbutton switches, multiple position switches, linear output Hall effect transducer ("Lohet" magnetic to voltage transducer), and potentiometer pedals allowing continuous adjustment of the controller signaling, or any combination of these devices.

The preferred wireless implementation is the Zigbee standard (IEEE 802.15.4). The wireless footswitch device can beneficially be used in a surgical operating room environment to control surgical or dental devices equipped with wireless transceivers. Examples of surgical devices that can benefit from wireless control according to the invention include, but are not limited to, oral drills, sagittal saws, reciprocating saws, oscillating saws, orthopedic drills, and burs and soft tissue resection and shaving devices. In the prior art these instruments often had buttons on the instruments themselves to control the operation of these instruments. However, it is beneficial to allow wireless footswitch control of these instruments, particularly during sensitive surgical and dental procedures, so that the operator does not move the instrument from its intended location in the act of depressing the button. Furthermore, for many procedures, such as endoscopic procedures, instrument operators may find it inconvenient to have to depress a button to activate an instrument using their hands. Accordingly, the prior art includes wired and wireless footswitch controlled devices.

The invention includes a wireless implementation for controlling devices that may be battery powered, and thus lack any wired connection, or for controlling devices that may be powered by a wired connection to an electric console. In both cases, the battery powered device or the electric console may include or be attached to a wireless transceiver for wireless communications between the device or console and the wireless footswitch. One embodiment of the invention includes a wireless footswitch adapter (WFSA) that may be connected to a conventional wired electric console. Replacing the wired connection to the conventional wired electric console with the WFSA allows wireless control of the electric console, thus freeing the operating room environment from a wired connection between the footswitch controller and the electric console. Alternatively, the WFSA may be integrated directly into an electric console.

The invention includes methods for syncing a wireless footswitch with a controlled device and/or WFSA and operating the controlled device and/or WFSA using a wireless footswitch. In this embodiment, the radiofrequency (RF) power from the wireless footswitch is adjusted to a low value during the syncing steps. By using lower power, the range of the wireless signal from the wireless footswitch is reduced relative to higher power signaling. This allows only controlled devices and WFSAs within a limited range to be synced to the wireless footswitch. Thus, for example, if multiple different WFSAs or controlled devices exist in adjacent operating rooms, the reduced power level for syncing allows the wireless footswitch to sync only to controlled devices and WFSAs in the same room as the footswitch, thus reducing the probability of (or preventing) unintended syncing with wireless devices in other rooms. Preferably, the RF power of the wireless footswitch during the syncing steps is adjusted to be high enough so that all controlled devices and WFSAs in the same room can be synced without bringing the devices or WFSAs in close proximity (e.g., a few inches) to the wireless footswitch, but low enough to reduce to probability of (or prevent) syncing with devices or WFSAs in adjacent rooms. Once the wireless footswitch has been synced to all of the devices and WFSAs that the user wants to control, the radiofrequency power is adjusted to provide higher power signaling. But because unwanted devices and WFSAs have not been synced to the wireless footswitch, there is no danger of unintentionally controlling those devices and WFSAs. Adjusting the wireless footswitch to a higher power for device and WFSA signaling ensures robust communication among the footswitch and devices and/or WFSAs, and reduces the likelihood of interference from any other nearby RF emitters.

FIG. 1 is a block diagram showing an embodiment of the invention with a WFSA and an electric console. In this embodiment, a transceiver in a three pedal footswitch 110 communicates wirelessly 120 with a transceiver in a WFSA 130. Preferably the wireless footswitch 110 is battery powered. The WFSA 130 is hardwired for communication 140 or may be integrally connected with an electric console 150. Communication 140 between the WFSA 130 and the electric console 150 allows transmission of the status of the footswitch (for example, which pedal is depressed and how far) to the electric console 150. The electric console 150 translates the status of the footswitch into electrical power signals transmitted through line 160 to a device such as a surgical instrument 170 in order to control the surgical instrument. Upon successful syncing with the WFSA, the wireless footswitch may send a signal to the WFSA, which may be passed to the electric console 150 for controlling an indicator, for example, a light emitting diode (LED) to indicate successful syncing to the user. Through commands from the wireless footswitch 110, the electric console 150 may control, for example, the speed and direction of a surgical drill, shaver, reamer, or saw, and/or pump for fluid removal.

The wireless footswitch 110 may be configured to control multiple devices 170 through electric console 150. In one embodiment, the syncing process involves setting the power level on a wireless transceiver in the wireless footswitch 110 to a lower power mode in order to communicate sync signals only with the WFSA 130 that is in the same room as the wireless footswitch 110. The syncing operation may be initiated, for example, by pressing a button on the WFSA 130 or on the wireless footswitch 110. After sync is complete, the transceiver in the wireless footswitch 110 may be set to a higher power mode for sending control signals and receiving status information form the electric console 150 through the WFSA 130. The wireless footswitch 110 may include a switch to allow a user to select among multiple devices 170 attached to the electric console 150. LED indicator lights on the WFSA 130 or the electric console 150 may be used to indicate to the user which of the multiple devices 170 is active and controllable with the wireless footswitch 110.

In one embodiment, the wireless footswitch 110 is a three pedal footswitch with pedals 112, 114, and 116. In this embodiment, pedal 112 is designated as the "forward" pedal used, for example, for driving the device 170 in a forward or clockwise direction; pedal 114 is designated as the "reverse" pedal used, for example, for driving the device 170 in a reverse or counterclockwise direction; and pedal 116 is designated as the "oscillate" pedal used, for example, for oscillating the device. Other switches and pedals not shown in FIG. 1 may be used for further control of device 170, for switching between controlled devices 170, for activating the sync function on the wireless footswitch, or any other desired functionality.

Figure 2:
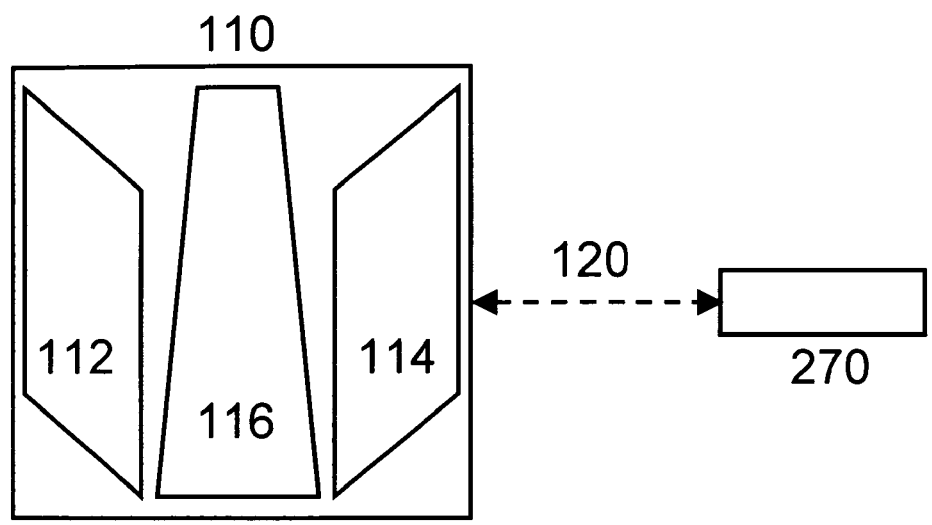
FIG. 2 is a block diagram showing an embodiment of the invention that includes a wirelessly controlled battery powered device.

FIG. 2 is a block diagram showing an embodiment of the invention that includes a wirelessly controlled battery powered device 270. In this embodiment, a wireless transceiver in the wireless footswitch 110 directly communicates with a wireless transceiver in a battery powered device 270 without the need for a WFSA or an electric console. The battery powered device 270 may be any device, for example, a surgical instrument such as a surgical drill, shaver, reamer, or saw. Preferably, the battery powered device 270 includes one or more rechargeable batteries.

In a preferred embodiment, the syncing operation between the wireless footswitch 110 and the battery powered device 270 is similar to that described above. First, lower powered wireless sync signals are sent between the wireless footswitch 110 and devices 270 such that only wireless devices 270 within a limited range will sync to the wireless footswitch 110. The syncing operation may be initiated, for example, by pressing a button on the devices 270. If multiple devices are to be controlled, the syncing operation will be repeated, for example by depressing a pushbutton switch on each of the devices 270, on the wireless footswitch 110, or both, for each of the devices 270 to be controlled. After every device 270 to be controlled is synced to the wireless footswitch, the wireless control signals may be sent using a higher power control signal mode. Which device 270 is controlled at any given time may be changed by the user, for example, by using a pushbutton switch on the wireless footswitch 110.

Figure 3:
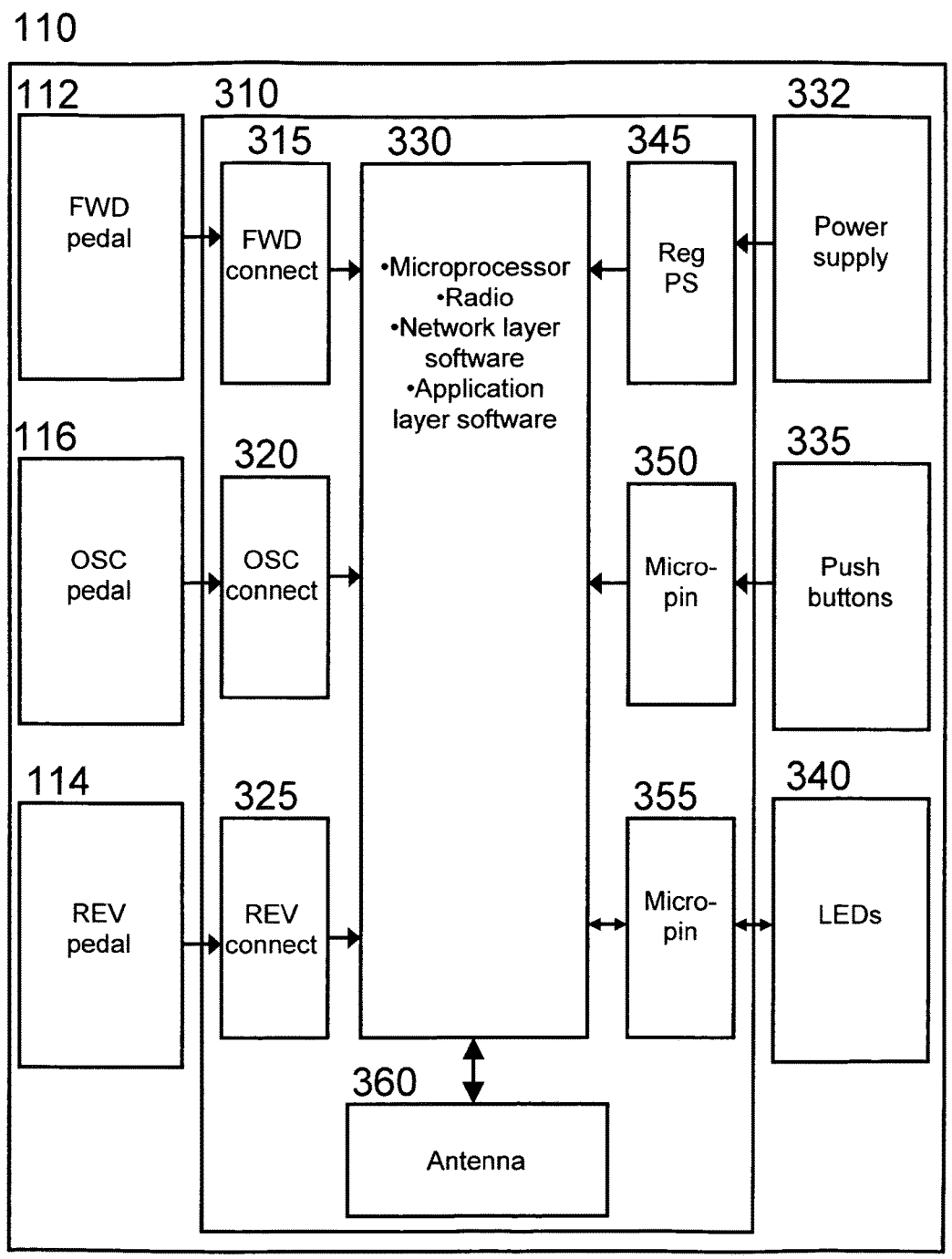
FIG. 3 is a block diagram showing an embodiment of the wireless footswitch.

FIG. 3 is a block diagram showing an embodiment of the wireless footswitch 110. This embodiment includes three pedals 112, 114, and 116, for forward, reverse, and oscillate operations, respectively. The term "pedal" includes, but is not limited to, any indicating device capable of converting a motion of the foot to a signal that can be transmitted. The pedals may include springs to force the pedals upwards when they are not being depressed and magnets for providing a signal indicating the degree of pedal depression. Each of the pedals is connected to connection circuitry 315, 320, and 325 on a printed circuit board 310 that includes a chipset 330. The connection circuitry 315, 320, and 325 may include magnetic sensors using, for example, the Lohet transducer, which can use the magnetic fields from the magnets in the pedals to determine the pedal position and convert the sensed pedal position to an analog voltage. The connection circuitry outputs the analog voltage corresponding to the pedal position to analog to digital (A/D) converters on the chipset 330.

This embodiment of the wireless footswitch 110 also includes a power supply 332, preferably batteries, which connects to an input 345 regulated power supply to provide regulated power to the chipset 330 and other powered circuitry on the footswitch 110. Pushbuttons 335 may include, for example, a connect/disconnect button and/or other buttons to facilitate control of multiple devices, as described above. The pushbuttons 335 connect to micro-pin inputs 350 to the chipset 330. LEDs 340, controlled by the chipset 330 through micro-pins 355, may include, for example, LEDs indicating sync to a controlled device or WFSA and for indicating low battery charge. LEDs 340 connect to micro-pin inputs 355 to the chipset 330.

The chipset 330 includes a microprocessor for processing inputs from the pedals 112, 114, and 116, any controlled devices 270 or WFSAs 130, and buttons 335, and for generating outputs to the wireless radio and LEDs 340. In a preferred embodiment, the wireless radio is a Freescale MC13213 chip. The chipset also includes memory, for example flash memory, that contains network layer software and application layer software. In a preferred embodiment, the network layer software is Freescale's Bee-Stack™ Zigbee codebase. The wireless radio is connected to an antenna 360 for sending and receiving the wireless (e.g., radiofrequency) signals from the wireless radio.

Figure 4:
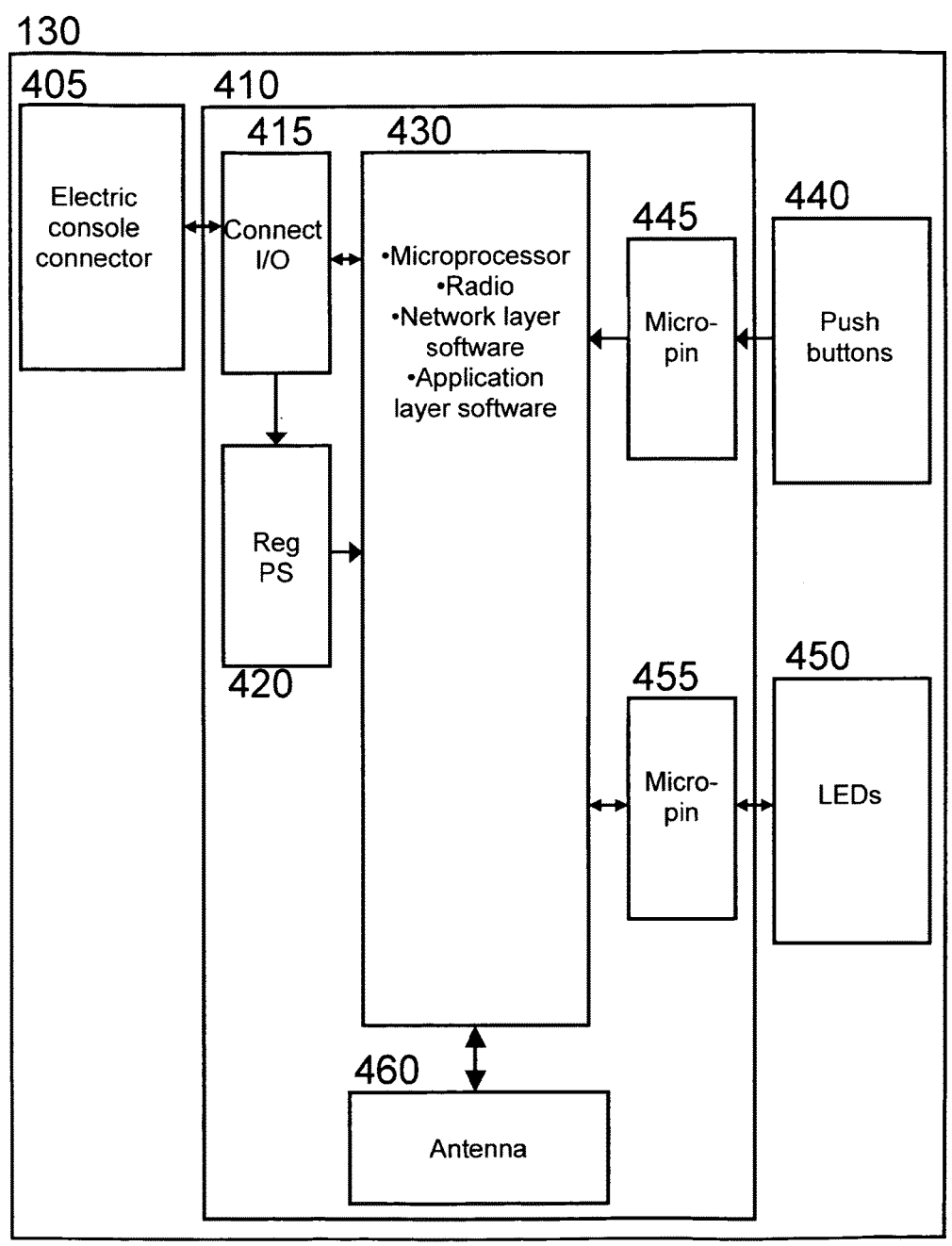
FIG. 4 is a block diagram showing an embodiment of the wireless footswitch adapter.

FIG. 4 is a block diagram showing an embodiment of the WFSA 130. This embodiment includes an electric console connector 405 connected to input/output (I/O) connection circuitry 415 on a printed circuit board 410 that includes a chipset 430. The electric console connector 405 and I/O connection circuitry 415 allows the WFSA to communicate with the electric console 150 for controlling devices 170. The I/O connection circuitry 415 provides signaling information between the chipset 430 and the electric console 150, and provides power from the electric console 150 to an input 420 regulated power supply to provide regulated power to the chipset 430 and other powered circuitry on the WFSA 130. The WFSA 130 may also include inputs in the form of push buttons 440, which connect to micro-pin inputs 445 to the chipset 430. The push buttons 440 may include, for example, a connect/disconnect button for signaling to the footswitch 110 to initiate a syncing operation, as described above. LEDs 450, controlled by the chipset 430 through micro-pin connections 455, may include LEDs indicating successful sync and/or indicating connections to one or more controlled devices 170.

The chipset 430 includes a microprocessor for processing inputs from the pushbuttons 440, wireless communications from the footswitch 110, and signaling from the electric console 150, for generating outputs to the wireless radio and LEDs 450, and for signaling to the electric console 150 for controlling the device 170. In a preferred embodiment, the wireless radio is a Freescale MC13213 chip. The chipset also includes memory, for example flash memory, that contains network layer software and application layer software. In a preferred embodiment, the network layer software is Freescale's Bee-Stack™ Zigbee codebase. The wireless radio is connected to an antenna 460 for sending and receiving the wireless (e.g., radiofrequency) signals from the wireless radio.

Figure 5:
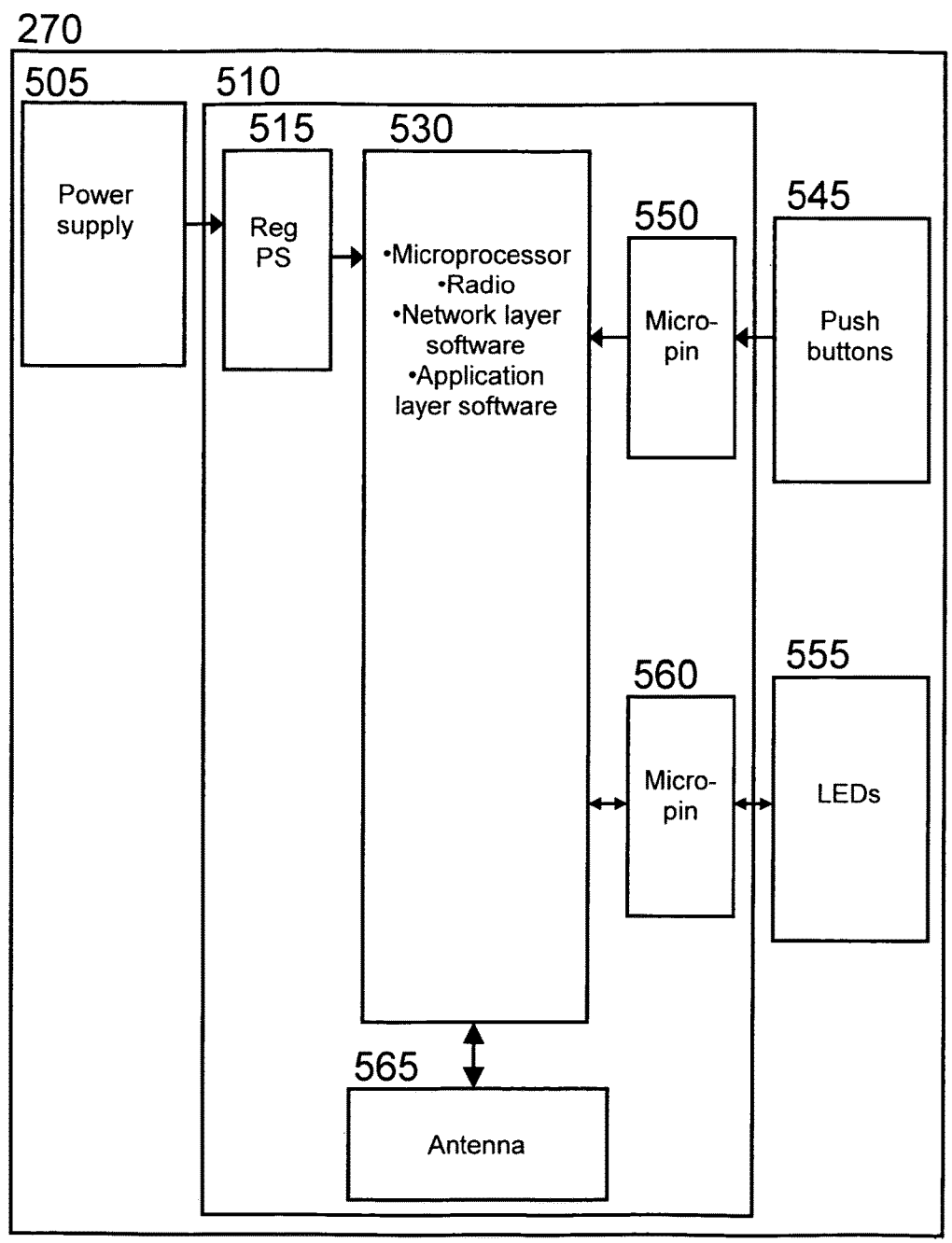
FIG. 5 is a block diagram of a wireless device that may be controlled by the wireless footswitch.

FIG. 5 is a block diagram showing an embodiment of a controlled device 270. This embodiment includes a power supply 505, preferably one or more rechargeable batteries. The power supply 505 supplies power to an input 515 regulated power supply on a printed circuit board 510 that includes a chipset 530. The regulated power supply circuitry 515 provides power to the chipset 530 and other powered circuitry on the controlled device 270. The controlled device 270 may include inputs in the form of push buttons 545, which connect to micro-pin inputs 550 to the chipset 530. The push buttons may include, for example, a connect/disconnect button for signaling to the footswitch 110 to initiate a syncing operation, as described above. LEDs 555 may include an LED indicating successful sync and a low battery charge level LED.

The chipset 530 includes a microprocessor for processing inputs from the pushbuttons 545 and wireless communications from the footswitch 110, and for generating outputs to the wireless radio and LEDs 450, and for controlling the operation of the device 270 itself. In a preferred embodiment, the wireless radio is a Freescale MC13213 chip. The chipset also includes memory, for example flash memory, that contains network layer software and application layer software. In a preferred embodiment, the network layer software is Freescale's Bee-Stack™ Zigbee codebase. The wireless radio is connected to an antenna 565 for sending and receiving the wireless (e.g., radiofrequency) signals from the wireless radio.

Figure 6:
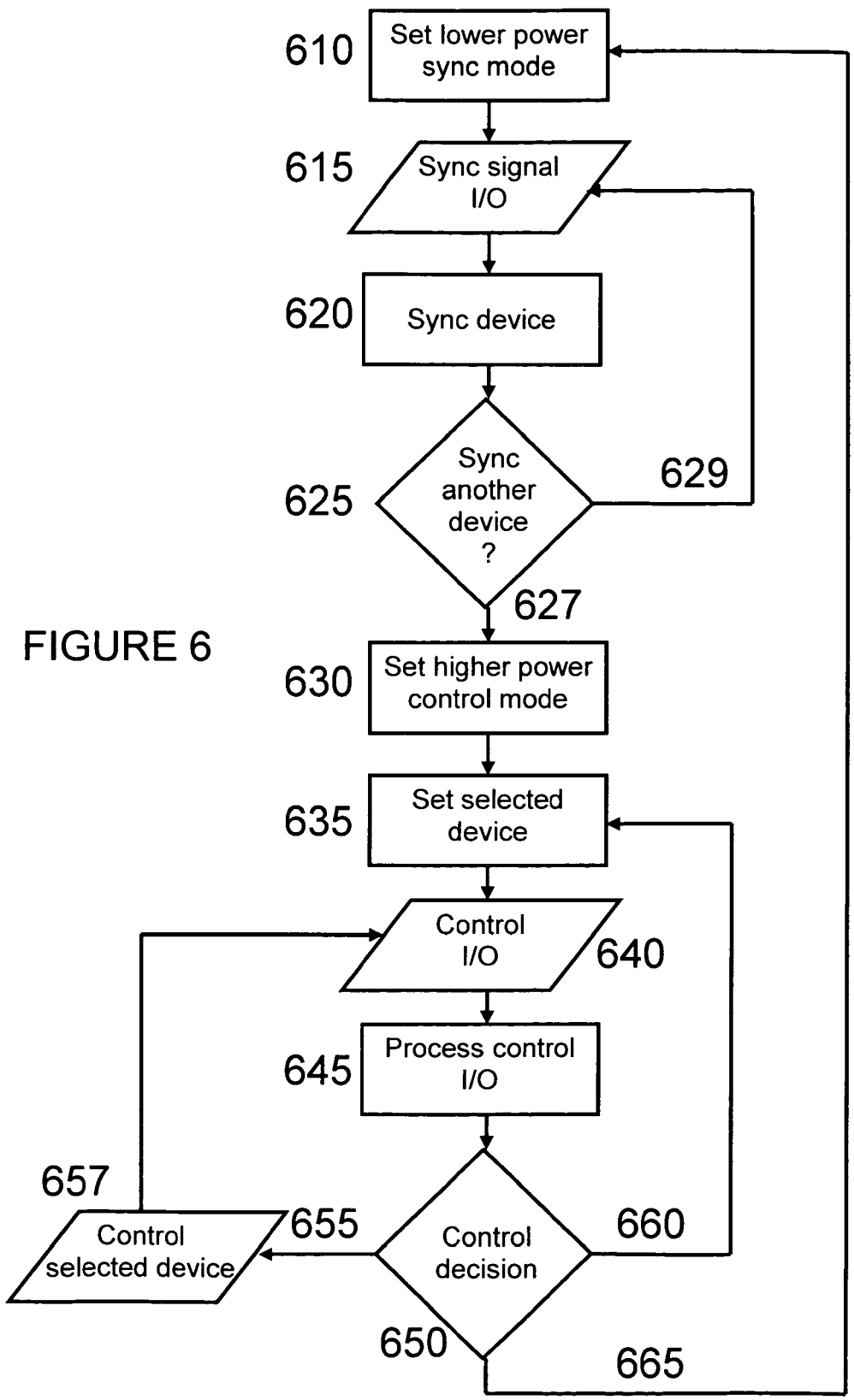
FIG. 6 is a flow diagram showing an embodiment of the methods of the invention.

FIG. 6 is a flow diagram showing an embodiment of a method of the invention. In step 610, the wireless footswitch 110 and any controlled devices 270 or WFSAs 130 are set to a lower power sync mode. This may be accomplished when a sync pushbutton on the footswitch, device, or WFSA is pushed, indicating the user's desire to sync the device or WFSA to the footswitch. In step 615, lower power sync signals are sent between the footswitch and the device or WFSA until the footswitch and device or WFSA are synced in step 620. Preferably, the lower power sync signals have sufficient power to sync with any device or WFSA in the same room as the wireless footswitch, but insufficient power to sync with any device or WFSA in adjacent rooms. Generally, the invention allows for adjusting the lower syncing power to a level that prevents syncing beyond a predetermined distance. Preferably, the lower power syncing signal power level is between about −16.2 dBm and −7.0 dBm. More preferably, the lower power signal is between about −10 dBm and −8.0 dBm. Even more preferably, the lower power signal is about −8.5 dBm. In step 625, the wireless footswitch determines whether another device is waiting to be synced 629, or proceeds 627 to the next step.

In step 630, the footswitch and controlled device or WFSA are set to a higher power control mode. Preferably, the higher power signal is between about −0.7 dBm and +1.4 dBm. Even more preferably, the higher power signal is about +1.4 dBm. If multiple devices are synced to the footswitch (whether individually or through the WFSA), the footswitch sets the device to be controlled in step 635. In this embodiment, the wireless footswitch itself is the network coordinator and is synced to multiple devices. Alternatively, the WFSA, electric console, or other device may be the network coordinator, with syncing between any of these alternative network coordinators and the controlled devices. The user provides input to the footswitch by depressing pedals or pushbuttons on the footswitch, or the footswitch receives wireless signals from the controlled devices and/or WFSA in step 640. In step 645, the footswitch processes the input from step 640 to determine in step 650 how to proceed. If the user depresses a pedal on the footswitch 655, the footswitch wirelessly signals the controlled device or WFSA in step 657 accordingly. The process then returns to step 640. If the user depresses a button on the footswitch (or a synced device or a synced WFSA) indicating the user's desire to switch the selected synced device to control 660, the process returns to step 635, where the new device is set for control. If the user depresses a button on the footswitch, an unsynced device, or an unsynced WFSA, indicating the user's desire to sync the unsynced device or WFSA 665, the process returns to step 610 to sync the new device or WFSA.

In a particularly preferred embodiment of the invention, the wireless footswitch remains in a lower power mode when it is inactive and/or not synced, thus preserving the battery life of the footswitch. After syncing, the wireless footswitch may enter the higher power mode to transmit status information and control signals during use. Also in a preferred embodiment, a first WFSA and/or battery powered controlled wireless device remains in a higher power mode and continuously scans for other WFSAs and controlled wireless devices. Upon detecting other WFSAs or controlled wireless devices, the first WFSA and/or controlled wireless device stores the channel (communication frequency) and network ID of the other WFSAs or controlled wireless devices in order to avoid using the same channel and/or network ID upon syncing the first WFSA or controlled wireless device with the wireless footswitch.

It will be understood by those skilled in the art that numerous improvements and modifications may be made to the embodiments of the invention discussed above without departing from the spirit and scope of the invention as defined by the following claims.

The invention claimed is:

1. A system for controlling the operation of a surgical device comprising:
   a first wireless transceiver configured to receive a connect signal while in a low power mode and, in response to the connect signal, to transmit low power wireless sync signals, and further configured to receive a wireless sync acknowledgement signal and to place the apparatus into a synced state,
   a pedal configured to be operated by a foot of a user and to provide a pedal signal, the first wireless transceiver further configured to generate, when the apparatus is in a synced state, a higher power mode wireless signal in response to the pedal signal, wherein the wireless signal controls the operation of the surgical device; and
   a wireless footswitch adapter with a second wireless transceiver;
   wherein syncing between the first and second transceivers is possible when the first transceiver is not in close proximity to second transceiver.

2. The system of claim 1, further comprising a sync button, wherein the sync button is configured to provide the connect signal to the first wireless transceiver.

3. The system of claim 1, wherein the surgical device comprises a sync button, wherein the sync button is configured to provide the connect signal to the first wireless transceiver.

4. The system of claim 3, wherein the second wireless transceiver remains in a higher power mode and monitors transmissions from a third wireless transceiver, and wherein after the second wireless transceiver detects a signal from the third wireless transceiver, the second wireless transceiver detects channel and network identification information from the third wireless transceiver, the channel and network identification information being excluded from the possible channels and network identifications available for use when syncing the second wireless transceiver to the first wireless transceiver.

5. The system of claim 1, wherein the first wireless transceiver is an IEEE 802.15.4 wireless transceiver using a ZIGBEE network stack communication protocol.

6. The system of claim 1, wherein the wireless footswitch adapter further comprises a sync button, wherein the sync button is configured to provide the connect signal to the first wireless transceiver.

7. The system of claim 6, wherein the second wireless transceiver remains in a higher power mode and monitors transmissions from a third wireless transceiver, and wherein after the second wireless transceiver detects a signal from the third wireless transceiver, the second wireless transceiver detects channel and network identification information from the third wireless transceiver, the channel and network identification information being excluded from the possible channels and network identifications available for use when syncing the second wireless transceiver to the first wireless transceiver.

8. The system of claim 6, further comprising an electric console for providing power and wired control signals to the surgical device, wherein the wireless footswitch adapter receives the higher power mode wireless signal in response to the pedal signal and transmits a wired signal representative of the higher power mode wireless signal to the electric console.

9. The system of claim 6, wherein the low power mode is adjusted to a power that allows syncing the wireless footswitch with the wireless footswitch adapter within a predetermined distance from the wireless footswitch and does not allow syncing the wireless footswitch with a wireless footswitch adapter beyond the predetermined distance, wherein the predetermined distance is greater than a close proximity and less than the distance between two rooms.

10. The system of claim 6, wherein the lower power mode is in the range of about −16.2 dBm and about −7.0 dBm and the higher power mode is in the range of about −0.7 dBm and about +1.4 dBm.

* * * * *